United States Patent

Graf et al.

[11] Patent Number: 5,980,576
[45] Date of Patent: Nov. 9, 1999

[54] METHOD OF PROVIDING PROSTHETIC SOCKETS AND TEMPORARY PROSTHETIC SOCKET

[76] Inventors: Peter M. Graf, 566 11th Ave., San Francisco, Calif. 94118; Richard M. Stess, 36 Dutch Valley La., San Anselmo, Calif. 94960

[21] Appl. No.: 09/032,719

[22] Filed: Feb. 27, 1998

[51] Int. Cl.$^6$ .............................. A61F 2/78; B29C 33/40
[52] U.S. Cl. ..................... 623/33; 264/222; 264/DIG. 30
[58] Field of Search ......................... 623/33–36; 264/222, 264/DIG. 30; 425/2

[56] References Cited

U.S. PATENT DOCUMENTS

| | | | |
|---|---|---|---|
| 1,351,789 | 9/1920 | Rowley . | |
| 1,907,511 | 5/1933 | Davies . | |
| 4,193,395 | 3/1980 | Gruber | 128/90 |
| 4,307,056 | 12/1981 | Meyer | 264/222 |
| 4,411,262 | 10/1983 | von Bonin et al. | 128/90 |
| 4,473,421 | 9/1984 | Gustafsson | 156/214 |
| 4,502,479 | 3/1985 | Garwood et al. | 128/90 |
| 4,667,661 | 5/1987 | Scholz et al. | 128/90 |
| 4,923,474 | 5/1990 | Klasson et al. | 623/33 |
| 5,228,164 | 7/1993 | Graf et al. | 12/133 |
| 5,258,036 | 11/1993 | Edenbaum et al. | 623/33 |
| 5,376,127 | 12/1994 | Swanson | 623/27 |
| 5,376,129 | 12/1994 | Faulkner et al. | 623/33 |
| 5,376,132 | 12/1994 | Caspers | 623/36 |
| 5,387,245 | 2/1995 | Fay et al. | 623/37 |
| 5,405,405 | 4/1995 | Love | 623/37 |
| 5,503,543 | 4/1996 | Laghi | 425/2 |
| 5,718,925 | 2/1998 | Kristinsson et al. . | |

OTHER PUBLICATIONS

Technical Manual entitled "IceCast Compact" Version 1.01.

*Primary Examiner*—Bruce E. Snow
*Attorney, Agent, or Firm*—Flehr Hohbach Test Albritton & Herbert

[57] ABSTRACT

A method of providing prosthetic sockets (30) for a patient's residual limb (21). While the residual limb (21) is swollen with post-trauma edema (22–25), a resin-impregnated temporary shell forming sock (52) is placed onto the edema-swollen residual limb (21). The resin is activated to cause it to harden into a temporary prosthetic shell (30), but prior to hardening of the resin, the sock (52) is conformed to the patient's edema-swollen limb (21). After swelling of the residual limb (21) has substantially dissipated, a permanent prosthetic socket conforming to the patient's unswollen residual limb (22b–25c) is formed and the temporary prosthetic socket (30) is replaced with the permanent prosthetic socket. A temporary prosthetic socket (30) is also disclosed in which a resin-hardened temporary sock (52) is bonded to a socket liner (49) over a prosthetic attachment assembly (48) in a configuration substantially conforming to the patient's residual limb (21) when in an edema-swollen (22–25) condition.

8 Claims, 2 Drawing Sheets

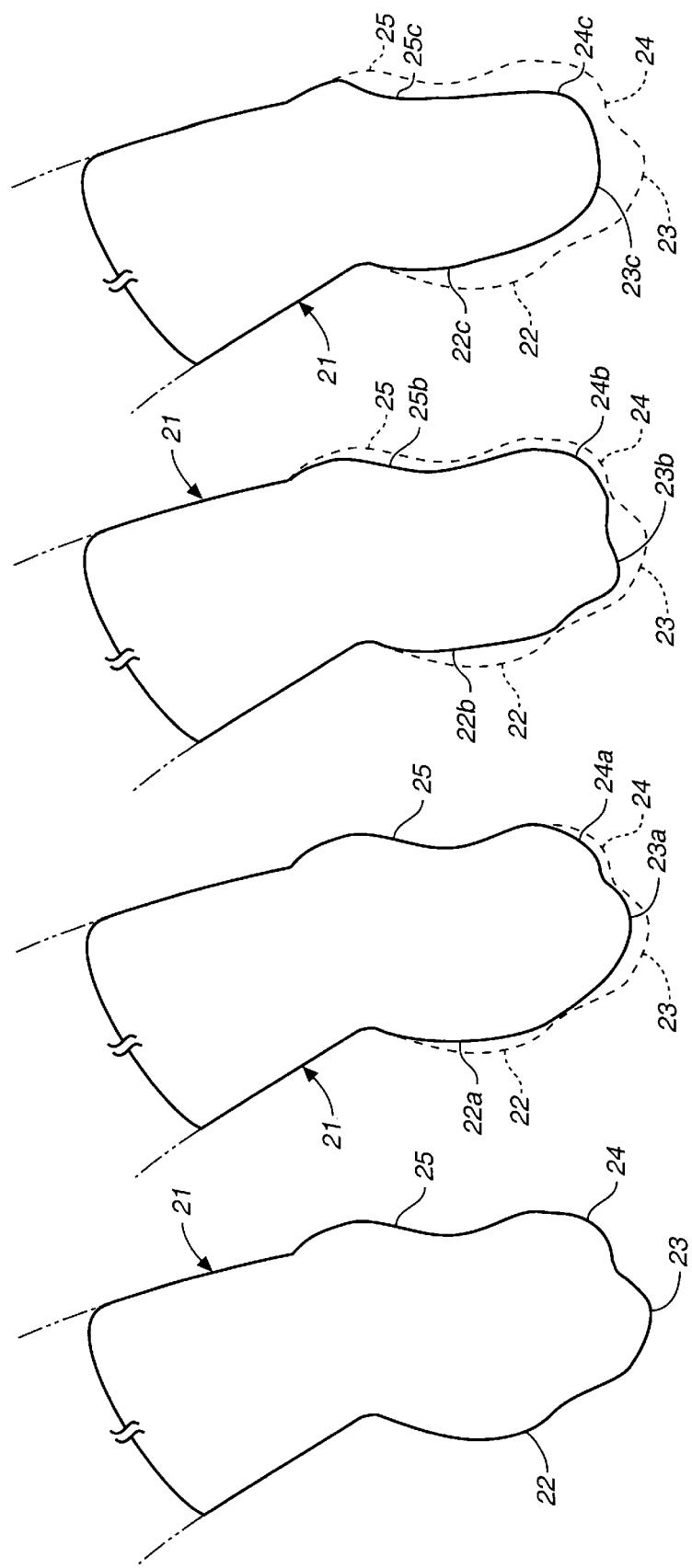

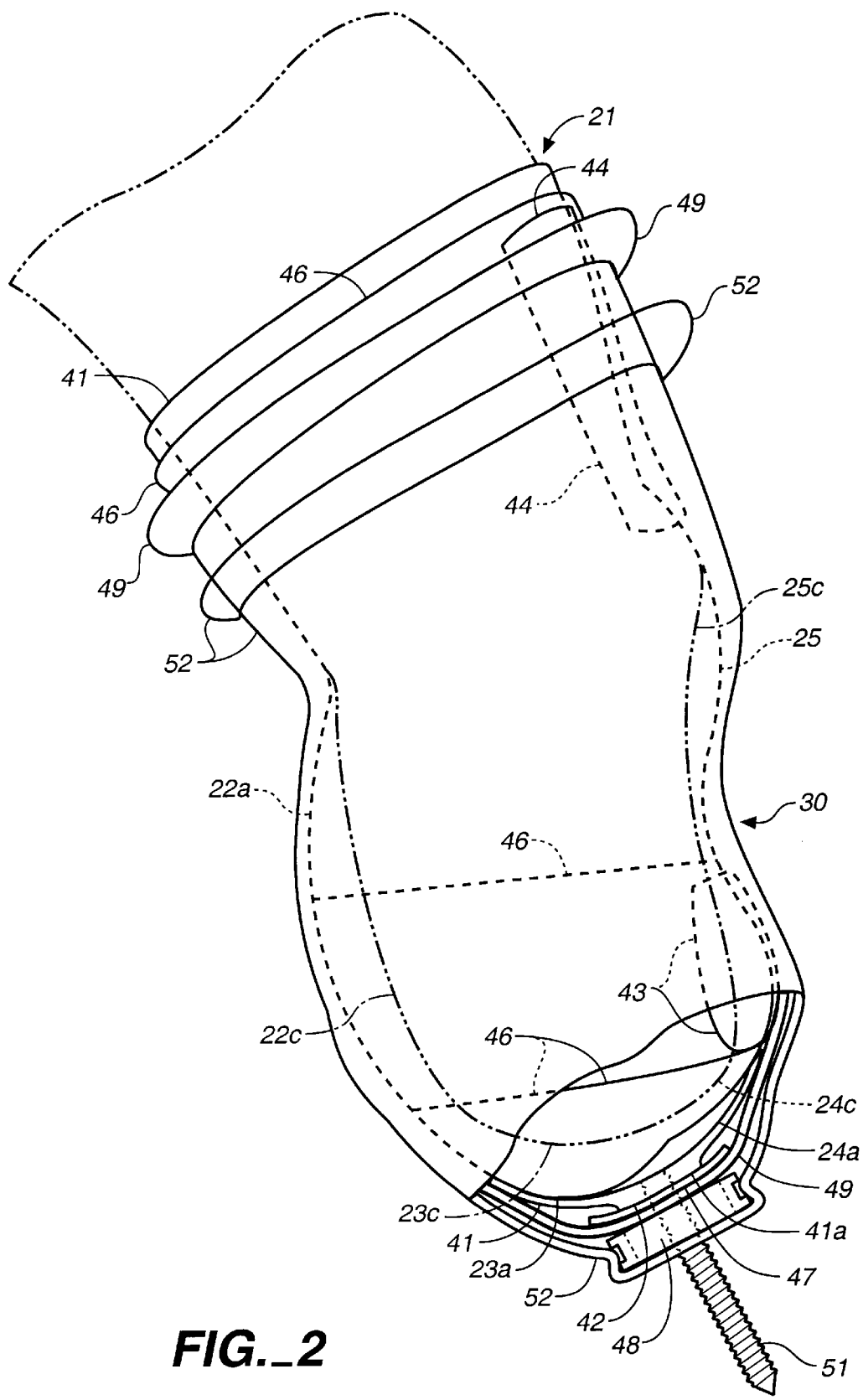
FIG._2

METHOD OF PROVIDING PROSTHETIC SOCKETS AND TEMPORARY PROSTHETIC SOCKET

TECHNICAL FIELD

The present invention relates to methods and apparatus for the formation of prosthetic devices, and more particularly, relates to the formation of prosthetic sockets which are used to support and connect prosthetic devices to the residual limbs of patients.

BACKGROUND ART

Prosthetic devices which are used to replace missing limbs are typically mounted by a socket to the residual limb or amputation stump of a patient. The sockets are most preferably custom made to conform to the configuration of the residual limb so as to be capable of supporting weight, in the case of a leg, or loading forces, in the case of an arm.

It has been found that it is highly desirable for patients to begin use of prosthetic devices as soon as possible after the required or accidental amputation of a limb. If a patient can be fitted with a prosthetic device soon after limb amputation, the prognosis for long term, effective use of the prosthetic is much higher. Additionally, the adverse psychological impact of an amputation can most effectively be minimized by rapid adaptation of the patient to a prosthetic in order to reinforce the patient's realization that he or she will be able to be self-sufficient.

While it is generally accepted that it is desirable to have patients begin using prosthetic devices soon after a limb amputation, there are serious practical difficulties in implementing such a procedure. Immediately after limb amputation, whether such amputation was a result of a planned surgical protocol or traumatic accidental occurrence, the residual limb or amputation stump will experience considerable post-operative or post-trauma edema or swelling. Such edema, of course, is also accompanied with considerable pain and discomfort. Even after the pain and discomfort subside to acceptable levels, the edema will continue for two to three months until the body gradually absorbs the fluids from the residual limb.

Since limb prosthetic devices are most typically mounted to a patient by a socket which is customized to the configuration of the patient's residual limb, formation of a prosthetic socket within a few weeks of limb amputation results in a socket which conforms to the configuration of the swollen or edema-affected residual limb.

One approach to forming prosthetic sockets, for example, is to form a plaster of Paris or other cast of the residual limb. The cast is removed from the limb and used in the laboratory as a negative. A positive plaster of Paris cast can be made from the negative and then a residual limb prosthetic socket built in the laboratory over the positive. Typical of prior art using this general approach are the systems described in U.S. Pat. Nos. 1,351,789; 1,907,511; 4,307,056; 4,473,421; 5,376,127; 5,376,129; 5,376,132; 5,405,405; and 5,503,543. These patents describe techniques of using a negative cast made from the residual limb as a basis for creating a customized prosthetic socket. Common to these various systems is the labor-intensive reality of making negatives, positives and thereafter forming a prosthetic socket on the positive. Accordingly, prosthetic sockets formed using such conventional techniques have been relatively expensive.

More recently, prosthetic systems have been devised which eliminate the need for formation of a negative of the residual limb. Rather than taking the negative to a laboratory, forming a positive and thereafter forming the socket, these techniques employ casting the socket in place directly on the patient's residual limb. Prior art showing this type of system includes U.S. Pat. Nos. 4,193,395; 4,923,474; 5,258,036; and 5,387,245.

One cast-in-place system is now commercially available in the United States under the ICEX trademark through Ossur USA, Inc. of Carpeteria, Calif. The Ossur USA system is described in detail in a manual entitled "IceCast Compact Technical Manual." Even such in-situ or cast-in-place systems, however, are very expensive.

The materials in the Ossur USA ICEX system, for example, will cost over $600, primarily because a carbon fiber sock is used to make a permanent (3 to 5 years) prosthetic socket.

The major problem which has occurred in prior art prosthetic socket casting procedures has been that, if the procedure is performed early, the resulting socket will reflect the edema or swelling in the residual limb. As the patient's body absorbs the edema, however, the swelling will subside, resulting in a poor fit between the prosthetic socket and the residual limb. Patients attempt to accommodate this edema absorption by adding additional socks over their residual limb before placing the limb in the prosthetic socket. The additional socks are used to fill the space left in the socket as a result of limb shrinking due to edema absorption. Since the edema will not generally be uniform and socks are uniform, the use of this technique is only partially satisfactory.

Two other approaches are taken to accommodate residual limb shrinkage. The first is to simply recast the socket, that is, to form a second prosthetic socket after the edema has dissipated, for example in two to three months. The second is to wait two to three months before forming the prosthetic socket. Both of these approaches have substantial disadvantages. The first is costly, while the second is undesirable in terms of the likelihood of the patient's successful adaptation to the prosthetic and psychological problems attendant to waiting.

Accordingly, it is an object of the present invention to provide a method for forming prosthetic sockets for patients' residual limbs which can be used during the post-operative or post-trauma period in which the patient's residual limb is swollen with edema.

Another object of the present invention is to provide a method and a temporary prosthetic socket which provides better conformance to the patient's residual limb.

Still a further object of the present invention is to provide a method and apparatus for forming prosthetic sockets which is relatively low in cost, minimizes pain and discomfort to the patient, and can be used with patients which have very substantial residual limb swelling.

The present invention has other objects and features of advantage which will become apparent from, or are set forth in more detail in, the accompanying drawings and the following Best Mode of Carrying Out the Invention.

DISCLOSURE OF INVENTION

The method of providing prosthetic sockets for a patient's residual limb of the present invention is comprised, briefly, of the steps of: while the residual limb is swollen with post-trauma edema, placing a resin impregnated, temporary shell-forming sock onto the edema-swollen residual limb; activating the resin in the sock to cause the resin and sock to harden into a temporary prosthetic socket; prior to hardening of the resin, conforming the socket to the patient's edema-swollen residual limb, preferably without applying sufficient pressure to the sock to substantially alter the configuration of the edema-swollen residual limb; after swelling in the residual limb has substantially dissipated, forming a permanent prosthetic socket to the patient's unswollen residual limb; and replacing the temporary prosthetic socket with the permanent prosthetic socket. In the preferred method a second temporary prosthetic socket is formed after edema swelling has reduced significantly from the level at which the first temporary prosthetic socket was formed.

In another aspect, a temporary prosthetic socket is provided which is comprised, briefly, of a socket liner formed to mount over a portion of the patient's residual limb; a prosthetic attachment assembly; and a resin-hardened fabric sock mounted over and bonded to the liner and secured to the prosthetic attachment assembly. The socket liner and resin-hardened sock substantially conform in configuration to the patient's residual limb when in an edema-swollen but unconstrained condition, and most preferably a lofted glass yarn sock with elastomeric fibers is employed.

BRIEF DESCRIPTION OF THE DRAWINGS

FIGS. 1A to 1D are side elevation, schematic views of a residual limb or amputation stump showing various post-trauma degrees of swelling.

FIG. 2 is an enlarged, side elevation, schematic view, partially broken away, of the residual limb of FIG. 1B with a temporary prosthetic socket in the process of being constructed in accordance with the method of the present invention.

BEST MODE OF CARRYING OUT THE INVENTION

The problems associated with making prosthetic sockets for residual limbs during the post-trauma period in which the limb experiences substantial swelling and edema, can be understood by reference to FIGS. 1A through 1D. In FIG. 1A a residual limb or amputation stump, generally designated 21, is shown, which in this case is a leg that has been amputated below the knee. It will be understood that the present method and apparatus are equally applicable to above-knee amputations and amputation to arms. In FIG. 1A residual limb 21 is shown soon after amputation, and includes edema-swollen areas 22, 23, 24 and 25. Notwithstanding the presence of such edema, it is highly desirable, as above set forth, to be able to have the patient begin walking with a prosthetic device. This requires that a residual limb's prosthetic socket be formed for attachment of a pylon and prosthetic foot assembly.

The prosthetic socket which is cast based upon residual limb 21, however, will conform to the residual limb including edema-swollen areas 22–25. Such a socket would be entirely suitable for use while the edema is still present in the residual limb, but as edema dissipates or is absorbed, the socket will no longer properly fit and support residual limb 21.

As can be seen from FIG. 1B residual limb 21 has experienced some shrinking. Thus, edema-swollen area 22 has reduced to area 22a, while the edema at 23 has dissipated to that shown at area 23a. The edema at area 24 has been absorbed to the volume shown at 24a, but the edema at area 25 remains substantially unchanged. Thus, in areas with edema, the absorption is not uniform and all areas of residual stump 21 do not include edema.

In FIG. 1C further edema absorption is shown at areas 22b, 23b and 25b. The final, unswollen configuration of residual limb 21 is shown in solid lines in FIG. 1D. Thus, areas 22c, 23c, 24c and 25c define the amputation stump in its final configuration. As will be seen from FIG. 1D the difference in configuration of residual limb 21 can be significant, although as schematically shown in FIG. 1B, 1C and 1D, the changes have been made somewhat larger in scale for purposes of illustration.

As will be appreciated, therefore, a prosthetic socket made for residual limb 21 in the condition of edema shown in FIG. 1A will not fit well for residual limb 21 as shown in FIG. 1D Depending upon the nature of the trauma and reason for amputation, the change from the immediate post-trauma event of FIG. 1A to the final unswollen residual limb condition of FIG. 1D can range from two to four months, and possibly longer. During this time, however, it is highly desirable for the patient to be using a limb prosthetic device. The method of the present invention enables the patient to have the advantages of a prosthetic device early after limb amputation.

In the method of the present invention, at least one, and often a plurality, of temporary prosthetic sockets are formed using relatively low-cost materials which are suitable for temporary use as a prosthetic socket. Moreover, the socket preferably is formed on the edema-swollen residual limb without applying sufficient pressure to the socket-forming materials so as to significantly alter the configuration of the edema-swollen residual limb. The resulting socket is then used for a relatively short period of time, for example, one month, and another prosthetic socket is made of the residual limb under a condition of reduced edema.

Referring to FIG. 2, therefore, a low-cost temporary prosthetic socket is shown as it is being made over the residual limb of FIG. 1B, including edema-swollen areas 22a, 23a, 24a and 25. After some period of time in which some edema has been absorbed, a prosthetic socket (not shown) made over the limb of FIG. 1A is discarded and a new casting is made of the residual limb, for example, when it is the condition as shown in FIG. 1B and FIG. 2. This temporary prosthetic socket, generally designated 30, can then be discarded and the process repeated after another period of time for the limb of FIG. 1C. Finally, the last temporary prosthetic socket is discarded and a final permanent prosthetic socket is formed of the limb of FIG. 1D, in its unswollen condition.

As will be appreciated, for some patients, only one temporary prosthetic socket needs to be formed before a final prosthetic socket is made from the unswollen limb of FIG. 1D. In other patients, two or even three temporary prosthetic sockets are made over the residual limb as the swelling of the limb recedes over time. Because none of the temporary sockets will be used for more than a month or two, the socket forming materials can be relatively low-cost and do not need to have the same structural strength and durability as would be required for a permanent prosthetic socket. Obviously, even "permanent" prosthetic sockets may have to be replaced after some period of time, for example, 3 to 5 years.

In the method of the present invention, it is preferred that the temporary prosthetic sockets be formed by casting the socket in place on the patient using a resin-impregnated sock that can set up or harden in a relatively short period of time, for example, 10 to 20 minutes. While broadly known in such prior art systems as the Ossur USA, Inc. system, in the method of the present invention, a temporary low-cost casting sock is employed. In the Ossur USA, Inc. system, a carbon fiber casting sock is used to form the socket on the residual stump because the socket is intended to be permanent or very long lasting.

In the method of the present invention, the casting sock which may be used does not have to last long. Thus, a lofted glass yarn sock with elastomeric fibers can be employed instead of a carbon fiber sock. This lofted glass yarn material is described in more detail in our U.S. Pat. No. 5,228,164, which is incorporated herein by reference, except that the socket forming sock of the present invention employs double the yarn density and thickness and is a ribbed knit, tuck stitched sock having a width of 5 inches. A corresponding increase in resin must be used relative to the sock of U.S. Pat. No. 5,228,164 in light of the greater sock yarn weight. This sock material and water activatable resin is commercially available through Minnesota Mining and Manufacturing of St. Paul Minn. The casting sock material of our patent had previously been used in preparing lasts for custom footwear, but in the present method and apparatus, it provides a low-cost system for the formation of a temporary prosthetic socket.

The prosthetic socket casting material of the present invention costs about $125, as opposed to the $600 cost for carbon fiber materials of the Ossur USA, Inc. system. The resultant socket is not as sturdy or durable as the prosthetic socket constructed using the Ossur USA system, but it is entirely satisfactory for use as a temporary prosthetic socket having a life on the order of one or two months.

While the present temporary prosthetic sockets can be formed by other techniques, casting them in place on the residual limb is advantageous in terms of conformance and in terms of keeping the cost low. The present method for casting the prosthetic socket in place will be briefly described, and it is based upon the process which is used by Ossur USA, Inc. in forming a permanent prosthetic socket, with three important changes. The first change is that the resin-impregnated sock material is a relatively low-cost lofted glass yarn with elastomeric fibers. The second change is that no special pylon attachment device needs to be secured to the casting sock, as is done with the Ossur carbon fiber sock. The third important difference is that conformance of the yarn to the residual limb need not be accomplished using a bladder and pump system.

The first step in casting a prosthetic socket in place on a residual limb is to mount a silicone liner 41 on the limb. Liner 41 includes a connector assembly or threaded plastic socket 42 at the closed end thereof, which is well known in the art and is used in the Ossur USA, Inc. ICEX system. The technician can then place padding over bony prominences, such as pads 43 and patella pad 44. Patella pad 44 is used to provide a channel permitting removal of the socket from the residual limb over the patella after hardening of the socket. The pads 43 and 44 can be held in place by a plastic wrap layer 46 so that the padding will not be permanently bound to the resulting socket.

A spacer disk 47 can be mounted over a post 51 threaded into attachment disk 42 provided on the silicone liner closed end. Next, a knit fabric liner 49 is rolled onto the residual limb and over the various pads, plastic wrap and spacer 47. Liner 49 has an opening in the end to allow passage of threaded post 51 therethrough. In the Ossur system, post 51 also is used to attach a bladder and pump, but they are not used in the present system. Pin 51 merely aligns and secures spacer 47 to the attachment disk 42 and the attachment assembly for the prosthetic pylon on the end of the silicone liner.

Next, an attachment coupling assembly 48 is mounted on post 51 over liner 49. The attachment device 48 typically will have a plurality of threaded bores which can receive fasteners that can be used to couple a prosthetic connector for the prosthetic pylon to the end of the resulting prosthetic socket. During casting, the threaded bores have screws in them so as to prevent the entry of resin into the bores during the casting procedure.

Finally, an elastic resin-impregnated lofted glass yarn knit sock 52 is soaked in water to commence activation of the water-activated resin. Once sock 52 is thoroughly soaked, it is rolled onto the residual limb over attachment coupling assembly 48. Sock 52 also has an opening to receive threaded pin 51, and additional water can be sprayed on sock 52 after it is unrolled onto limb 21 to insure activation. Silicone liner 41, knit fabric sock 49 and resin-impregnated fabric sock 52 preferably are all at least slightly resilient. Thus, they tend to conform to the configuration of residual limb 21, including edema-swollen areas 22a, 23a, 24a and 25. However, instead of using a bladder and pump to apply 70 to 100 millimeters of mercury pressure, as is done in the Ossur USA system, in the present method, the prosthetic technician merely manually smooths and eases the sock over the residual limb and its swollen areas. Thereafter, plastic wrap can be used to cover the sock and a resilient strip of material, such as a resilient bandage (ACE Bandage, for example) can be wrapped around the sock to urge the sock fibers together and to conform the sock to the residual limb, including the edema-swollen areas, without altering or changing the limb configuration in a manner which would produce pressure concentrations once the prosthetic is hardened. In formation of permanent prosthetic sockets, higher bladder-induce pressures insure that the carbon fibers are urged into closer proximity for greater strength and durability, but in a temporary prosthesis, that is not required, but can be used if desired.

About 10 to 20 minutes is required for a water-activated resin to harden sufficiently to enable a prosthetic socket or shell to be formed. Once hardened, the resilient wraps and plastic can be removed from the outside of the socket, post 51 can be removed, and the prosthetic shell can be pulled off of silicone liner 41. The resin-hardened sock material 52 at the area of post 51 can be ground down to expose the attachment assembly 48, and the temporary fasteners in assembly 48 can be removed so that the prosthetic pylon can be attached to the socket by attachment assembly 48. The resin in the casting sock 52 will have bound to the socket liner material 49 and will mechanically trap the pylon attachment device 48 in the end of the socket. As can be seen from FIG. 2, attachment member 48 also can have ridges in the sides thereof to assist in locking with hardened sock 52. Once the shell has been removed, the silicone liner 41 can also be removed from residual stump 21.

The result is a cast, temporary prosthetic socket which substantially conforms in configuration to the patient's residual limb when in an edema-swollen condition. As will be seen from FIG. 2, such a socket will conform to the edema-swollen areas 22a, 23a, 24a and 25, and will be usable until the swelling has dissipated or been absorbed. The eventual residual limb configuration is shown at phantom lines 22c through 25c, and when swelling has substantially disappeared, a permanent prosthetic socket can be formed on this final configuration of the residual limb using, for example, the process and apparatus of the Ossur USA, Inc. system.

The method and apparatus of the present invention allow patients to begin using prosthetic devices well before edema in their residual limb has been absorbed. The result is more effective use of their prosthetic device, as well as greater patient confidence and mental well-being.

What is claimed is:

1. A method of providing prosthetic sockets for a patient's residual limb comprising the steps of:

while said residual limb is swollen with post-trauma edema, rolling a temporary shell-forming lofted glass yarn sock with a water-curable resin carried thereby onto the edema-swollen residual limb;

actuating the resin in said sock by contacting said sock with water to cause said resin and sock to harden into a temporary prosthetic socket;

prior to hardening of said resin, conforming said sock to the patient's edema-swollen residual limb by wrapping said sock with an elastic strip;

after swelling in said residual limb has substantially dissipated, forming a permanent prosthetic socket conforming to the patient's unswollen residual limb; and replacing said temporary prosthetic socket with said permanent prosthetic socket.

2. The method as defined in claim 1 wherein, said rolling step is accomplished by rolling a ribbed, knit, tuck stitched yarn sock having elastomeric fibers therein.

3. The method as defined in claim 2 wherein, said conforming step is accomplished while said resin is hardening.

4. The method as defined in claim 1, and the steps of:

prior to said rolling step positioning a socket liner on said edema-swollen residual limb;

during said rolling step, rolling said sock onto said residual limb over said socket liner; and during hardening of said resin, bonding said sock to said socket liner with said resin with a prosthetic attachment assembly therebetween.

5. The method as defined in claim 1 wherein, said step of forming a permanent prosthetic socket is accomplished by casting said prosthetic socket in place on the patient's unswollen residual limb.

6. The method as defined in claim 1, and the steps of:

prior to dissipation of all the swelling in said residual limb, forming a second temporary prosthetic socket over said residual limb while said residual limb is in a reduced state of swelling; and replacing said temporary prosthetic socket with said second temporary prosthetic socket.

7. The method as defined in claim 6 wherein, said step of forming a second temporary prosthetic socket is accomplished by manually conforming a resin-impregnated shell-forming sock to said residual limb while in said reduced state of swelling, and hardening said resin while conformed to said residual limb.

8. A method of providing prosthetic sockets for a patient's residual limb comprising the steps of:

while said residual limb is swollen with post-trauma edema, forming a temporary prosthetic socket by rolling a lofted glass yarn knit sock with water-curable resin therein onto said residual limb, manually manipulating said sock while on said residual limb to conform to the edema-swollen rendered limb, contacting said sock with water to cure said resin, and wrapping said sock with an elastic strip during hardening of said resin;

after swelling in said residual limb has substantially dissipated, forming a permanent prosthetic socket conforming to the patient's unswollen residual limb; and replacing said temporary prosthetic socket with said permanent prosthetic socket.

* * * * *